United States Patent [19]
Grillo et al.

[11] Patent Number: 5,882,707
[45] Date of Patent: Mar. 16, 1999

[54] METHOD OF COATING AN EDIBLE SUBSTRATE WITH SUGAR/SYRUP OR SUGARLESS SOLUTIONS CONTAINING DRY COLOR CONCENTRATE

[75] Inventors: Susan M. Grillo, Lansdale; Kathleen Saraceni, North Wales; Julie A. Kelley, Huntingdon Valley, all of Pa.

[73] Assignee: BPSI Holdings, Inc., Wilmington, Del.

[21] Appl. No.: 583,401

[22] Filed: Jan. 5, 1996

[51] Int. Cl.⁶ ............................................ A23L 1/09
[52] U.S. Cl. .................... 426/302; 426/305; 426/540; 426/658; 426/443; 424/474; 424/479
[58] Field of Search ................................. 426/262, 302, 426/305, 540, 658, 443; 424/474, 479

[56] References Cited

U.S. PATENT DOCUMENTS

| | | | |
|---|---|---|---|
| 3,769,027 | 10/1973 | Mangiere et al. | 426/240 X |
| 4,582,709 | 4/1986 | Peters et al. | 426/74 |
| 4,643,894 | 2/1987 | Porter et al. | 424/479 |
| 5,411,746 | 5/1995 | Signorino et al. | 424/464 |

*Primary Examiner*—Milton Cano
*Attorney, Agent, or Firm*—John F. A. Earley; John F. A. Earley, III; Harding, Earley, Follmer & Frailey

[57] ABSTRACT

A dry color concentrate for use in coloring sugar/syrup solutions and sugarless syrup solutions used to coat confectionery forms, pharmaceutical tablets, and the like, comprises 1) a carbohydrate selected from the group consisting of corn syrup solids, maltodextrin, tapioca dextrin, sugar, polyols, and combinations thereof, 2) a colorant, and, optionally, 3) a plasticizer.

63 Claims, No Drawings

METHOD OF COATING AN EDIBLE SUBSTRATE WITH SUGAR/SYRUP OR SUGARLESS SOLUTIONS CONTAINING DRY COLOR CONCENTRATE

BACKGROUND OF THE INVENTION

1. Field of the Invention

This invention relates to the field of coloring confectionery forms, pharmaceutical tablets, and the like, and specifically is concerned with a dry color concentrate for use in coloring sugar/syrup solutions used to coat confectionery forms, pharmaceutical tablets, and the like. Further, the invention specifically is concerned with a dry color concentrate for use in coloring sugarless syrup solutions used to coat confectionery forms, pharmaceutical tablets, and the like.

2. Description of the Prior Art

Generally, known color concentrates used in the food/confectionery industry are liquids. Such liquid color concentrates suffer from warehousing problems caused by storing liquids, such as susceptibility to changes because of heat, cold and bacteria, and shelf-life problems caused by the solvent in the liquid color concentrate.

SUMMARY OF THE INVENTION

It is an object of the invention to provide a coloring concentrate for use in coloring sugar/syrup solutions and sugarless syrup solutions used to coat confectionery forms, pharmaceutical tablets, and the like, which eliminates warehousing problems caused by storing liquid color concentrates, such as susceptibility to changes because of heat, cold and bacteria, and also eliminates shelf-life problems caused by the solvent in the liquid color concentrate.

These and other objects of the invention are accomplished by our invention, which is described below.

DETAILED DESCRIPTION OF THE INVENTION

In accordance with the invention, a dry color concentrate for use in coloring sugar/syrup solutions and sugarless syrup solutions used to coat confectionery forms, pharmaceutical tablets, and the like comprises a carbohydrate and a colorant. Optionally, the dry color concentrate may include a plasticizer.

The invention also includes a clear or colorless dry concentrate for mixing into a sugar/syrup solution or a sugarless syrup solution used to coat confectionery forms, pharmaceutical tablets, and the like, which comprises a carbohydrate, and optionally a plasticizer.

Further, the invention includes a method of enhancing a sugar/syrup solution or a sugarless syrup solution used to coat confectionery forms, pharmaceutical tablets, and the like, which comprises the steps of providing a carbohydrate, and mixing the carbohydrate into a sugar/syrup solution to form an enhanced sugar/syrup solution, or mixing the carbohydrate into a sugarless syrup solution to form an enhanced sugarless syrup solution. Optionally, a plasticizer may be mixed together with the carbohydrate before the carbohydrate is mixed into the sugar/syrup solution or the sugarless syrup solution. Alternatively, a plasticizer may be mixed into the sugar/syrup solution or the sugarless syrup solution before, during, or after the carbohydrate is mixed into the sugar/syrup solution or the sugarless solution.

The invention also includes a method of coloring a sugar/syrup solution or a sugarless syrup solution used to coat confectionery forms, pharmaceutical tablets, and the like, which comprises the steps of mixing a carbohydrate and a colorant together to form a dry color concentrate, and mixing the dry color concentrate into a sugar/syrup solution to form a colored sugar/syrup solution, or mixing the dry color concentrate into a sugarless syrup solution to form a colored sugarless syrup solution. Optionally, a plasticizer may be mixed together with the carbohydrate before the carbohydrate is mixed into the sugar/syrup solution or the sugarless syrup solution. Alternatively, the carbohydrate, the colorant, and optionally, the plasticizer may be individually mixed into the sugar/syrup solution or the sugarless syrup solution to form the colored sugar/syrup solution or the colored sugarless syrup solution, rather than first pre-mixed together to form a dry color concentrate.

Also, the invention includes a method of coating confectionery forms, pharmaceutical tablets, and the like, which comprises the steps of mixing a dry concentrate comprising a carbohydrate with a sugar/syrup solution or a sugarless syrup solution to form a coating solution, applying the coating solution to a substrate such as confectionery forms, pharmaceutical tablets, and the like, to form a coating thereon, and drying the coating. The dry concentrate may also include a colorant, a plasticizer, or both a colorant and a plasticizer. Alternatively, the method of coating may comprise mixing the carbohydrate, and, optionally, the colorant, or the plasticizer, or both the colorant and the plasticizer, into the sugar/syrup solution or the sugarless syrup solution without first forming a dry concentrate to form a coating solution without first forming a dry concentrate, applying the coating solution to the substrate to form a coating thereon, and drying the coating.

The carbohydrate acts to enhance the sugar/syrup solution and the sugarless syrup solution by lending opacifying and strength properties. The carbohydrate may be corn syrup solids, and preferably, corn syrup solids having a dextrose equivalent (DE) of 24 to 43, such as FRODEX 24D corn syrup solids made by American Maize-Products Company. Alternatively, maltodextrin, such as STAR DRI 15 maltodextrin made by Staley, may be used. Other examples of the carbohydrate include tapioca dextrin, dextrose, sugar, and sugar alcohols or polyols such as sorbitol, maltitol, xylitol, and mannitol. The carbohydrate of the invention also may comprise of combinations of the above-mentioned carbohydrates. Corn syrup solids are the preferred enhancer.

The colorant may be any approved colors, opacifiers, or dyes. For example, the colorant may be FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, and dyes and combinations thereof.

Examples of the plasticizer include glycerin, polyethylene glycol 8000, triacetin, and lecithin. Other examples of plasticizers include those recited in Colorcon U.S. Pat. No. 4,543,370 issued on Sep. 24, 1995, which is incorporated herein by reference. Glycerin is preferred.

The ranges for each component of the dry concentrate are as follows, by weight:

|  | Acceptable Ranges | Preferred Ranges |
| --- | --- | --- |
| carbohydrate (i.e., corn syrup solids) | 12% to 100% | 35% to 65% |
| plasticizer (i.e., glycerin) | 0% to 81% | 5% to 6% |
| colorants | 0% to 81% | 35% to 65% |

The sugar/syrup solution generally comprises a mixture of sugar in water at a concentration by weight of about 70% sugar. However, the sugar concentration may be varied as desired. Typically, the sugar/syrup solution has a sugar concentration between 65% and 75%. Likewise, the sugarless syrup solution generally comprises a mixture of polyols in water at a concentration by weight of about 70% polyol. However, the polyol concentration may be varied as desired. Typically, the sugarless solution has a polyol concentration between 65% and 75%.

We now turn to the examples of the invention, all ingredients being by weight.

EXAMPLE 1

The following ingredients are dry blended together in a mixer, such as a PK blender, for about 5 minutes to form a dry concentrate:

| Component | Percentages | Grams |
| --- | --- | --- |
| Corn syrup solids (24 DE) | 54.28 | 814.20 |
| FD & C Yellow No. 6 HT (38%–42%) | 32.62 | 489.30 |
| Titanium Dioxide | 10.00 | 150.00 |
| FD & C Red No. 4 HT (38%–42%) | 3.1 | 46.50 |
| | 100.00 | 1500.00 |

16.5 grams of the dry concentrate are mixed into 500 grams of a sugar/syrup solution in a lighting mixer for about 20 minutes, and the resulting coating composition is then applied by ladling or spraying onto 3000 grams of confectionery forms such as candy and the like and dried, resulting in confectionery forms having a vibrant color and an elegant coating.

The sugar/syrup solution has the following formulation, and is prepared by adding 2800 grams of sugar to 1200 grams of water. The solution is heated and stirred until boiling. When boiling is reached, the solution is removed from heat and allowed to cool to an appropriate temperature for use. Chocolate confectionery forms require a solution temperature of about room temperature, while a hard candy may be coated at higher temperatures.

| Component | Percentages | Grams |
| --- | --- | --- |
| Sucrose | 70.000 | 2800.00 |
| Water | 30.000 | 1200.00 |
| | 100.000 | 4000.00 |

EXAMPLE 2

The following illustrates a sub-coat formulation of the dry color concentrate, the dry sub-coat formulation being used to enhance a sugar/syrup solution to be applied to substrates such as confectionery forms, pharmaceutical tablets, and the like, as a sub-coat before an overcoat or finishing coat is applied to the substrates:

| Component | Percentages | Grams |
| --- | --- | --- |
| Corn syrup solids (FRODEX 24) | 50% | 750.00 |
| Titanium Dioxide | 44% | 660.00 |
| Glycerin | 6% | 90.00 |
| | 100% | 1500.00 |

In this example, 83 grams of the sub-coat formulation is mixed into 600 grams of a 70% sugar solution made in accordance with the sugar solution of Example 1, and the resulting coating composition is applied to 3000 grams of confectionery forms such as chocolate, by ladling or spraying, and dried, resulting in confectionery forms having an excellent white opaque sub-coat that is ready to color coat.

EXAMPLE 3

In this example, it is desired to provide a clear coat to confectionery forms. Accordingly 16.5 grams of corn syrup solids are mixed into 500 grams of a 70% sugar/syrup solution made in accordance with the sugar solution of Example 1 to form an enhanced coating solution. The enhanced coating solution is then applied to 3000 grams of confectionery forms by ladling or spraying, and the applied coating is then dried on the confectionery forms resulting in confectionery forms having an excellent enhanced clear coating.

The following Examples 4 to 17 further illustrate the invention, all ingredients being by weight. The ingredients of each formulation are mixed together, and then added to a sugar/syrup solution to form an enhanced coating solution, which is applied to substrates such as confectionery forms, pharmaceutical tablets, and the like, and dried, as in Example 1, resulting in substrates having vibrant colors and an elegant coating.

EXAMPLE 4

| Component | Percentage | Grams |
| --- | --- | --- |
| Frodex 24D-Corn Syrup Solids | 59.00 | 354.00 |
| FD & C Yellow #5 HT (25%) | 21.00 | 126.00 |
| FD & C Yellow #5 HT (38%) | 4.00 | 24.00 |
| Titanium Dioxide | 10.00 | 60.00 |
| Glycerin | 6.00 | 36.00 |
| | 100.00 | 600.00 |

EXAMPLE 5

| Component | Percentage | Grams |
| --- | --- | --- |
| Frodex 24D-Corn Syrup Solids | 48.28 | 96.56 |
| FD & C Yellow #6 HT (38%) | 32.92 | 65.84 |
| FD & C Red #40 HT (39%) | 2.80 | 5.60 |
| Titanium Dioxide | 10.00 | 20.00 |
| Glycerin | 6.00 | 12.00 |
| | 100.00 | 200.00 |

EXAMPLE 6

| Component | Percentage | Grams |
| --- | --- | --- |
| Frodex 24D-Corn Syrup Solids | 45.04 | 270.24 |
| FD & C Red #40 HT (40%) | 32.20 | 193.20 |
| FD & C Yellow #5 HT (38%) | 6.32 | 37.92 |
| Titanium Dioxide | 6.24 | 37.44 |
| FD & C Blue #1 HT (31%) | 4.20 | 25.20 |
| Glycerin | 8.00 | 36.00 |
| | 100.00 | 600.00 |

EXAMPLE 7

| Component | Percentage | Grams |
|---|---|---|
| Maltodextrin | 54.28 | 814.20 |
| FD & C Yellow No. 6 HT (38%–42%) | 32.62 | 489.30 |
| Titanium Dioxide | 10.00 | 150.00 |
| FD & C Red No. 40 HT (38%–42%) | 3.10 | 46.50 |
| | 100.00 | 1500.00 |

EXAMPLE 8

| Component | Percentage | Grams |
|---|---|---|
| Tapioca Dextrin | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
| | 100.000 | 500.00 |

EXAMPLE 9

| Component | Percentage | Grams |
|---|---|---|
| Star Dri 1 Maltodextrin | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
| | 100.000 | 500.00 |

EXAMPLE 10

| Component | Percentage | Grams |
|---|---|---|
| Sugar | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
| | 100.000 | 500.00 |

EXAMPLE 11

| Component | Percentage | Grams |
|---|---|---|
| Dextrose | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.00 | 50.00 |
| | 100.000 | 500.00 |

EXAMPLE 12

| Component | Percentage | Grams |
|---|---|---|
| Maltisorb (Dry Maltitol Powder) | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
| | 100.000 | 500.00 |

EXAMPLE 13

| Component | Percentage | Grams |
|---|---|---|
| Corn Syrup Solids | 49.800 | 271.40 |
| Glycerin | 5.000 | 25.00 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
| | 100.000 | 500.00 |

EXAMPLE 14

| Component | Percentage | Grams |
|---|---|---|
| PEG 8000 | 81.00 | 405.00 |
| FRODEX 24D- Corn Syrup Solids | 12.00 | 60.00 |
| FD & C Yellow #6 HT (38%–42%) | 7.00 | 35.00 |
| | 100.00 | 500.00 |

EXAMPLE 15

| Component | Percentage | Grams |
|---|---|---|
| Frodex (Corn Syrup Solids) | 55.14 | 55.14 |
| Star Dri 1 (Maltodextrin) | 16.50 | 16.50 |
| Glycerin | 5.50 | 5.50 |
| FD & C Yellow #6 HT (38%–42%) | 16.46 | 16.46 |
| FD & C Red #40 HT (38%–42%) | 1.40 | 1.40 |
| Titanium Dioxide | 5.00 | 5.00 |
| | 100.00 | 100.00 |

EXAMPLE 16

| Component | Percentage | Grams |
|---|---|---|
| Frodex (Corn Syrup Solids) | 55.14 | 55.14 |
| Star Dri 1 (Maltodextrin) | 16.50 | 16.50 |
| Triacetin | 3.00 | 3.00 |
| Lecithin (Alcolec F100) | 2.50 | 2.50 |
| FD & C Yellow #6 HT (38%–42%) | 16.46 | 16.46 |
| FD & C Red #40 HT (38%–42%) | 1.40 | 1.40 |
| Titanium Dioxide | 5.00 | 5.00 |
| | 100.00 | 100.00 |

EXAMPLE 17

| Component | Percentage | Grams |
|---|---|---|
| Frodex (Corn Syrup Solids) | 57.64 | 57.64 |
| Star Dri 1 (Maltodextrin) | 16.50 | 16.50 |

-continued

| Component | Percentage | Grams |
|---|---|---|
| FD & C Yellow #6 HT (38%–42%) | 16.46 | 16.46 |
| FD & C Red #40 HT (38%–42%) | 1.40 | 1.40 |
| Titanium Dioxide | 5.00 | 5.00 |
| Triacetin | 3.00 | 3.00 |
|  | 100.00 | 100.00 |

The following Examples 18–20 further illustrate the invention, all ingredients being by weight. The ingredients of each formulation are mixed together, and then added to a sugarless syrup solution to form an enhanced coating solution, which is applied to substrates such as confectionery forms, pharmaceutical tablets, and the like, and dried, as in Example 1 except that the dry concentrate is mixed into a sugarless syrup solution rather than into a sugar/syrup solution, resulting in substrates having vibrant colors and elegant coatings.

EXAMPLE 18

| Component | Percentage | Grams |
|---|---|---|
| Sorbitol | 58.40 | 271.40 |
| FD & C Yellow #6 HT (38%–42%) | 32.62 | 163.10 |
| FD & C Red #40 HT (38%–42%) | 3.10 | 15.50 |
| Titanium Dioxide | 10.00 | 50.00 |
|  | 100.00 | 500.00 |

The sugarless syrup solution of this example is a 70% sorbitol solution (70% sorbitol and 30% water).

EXAMPLE 19

| Component | Percentage | Grams |
|---|---|---|
| Dextrose | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
|  | 100.000 | 500.00 |

The sugarless syrup solution of this example is a 70% dextrose solution (70% dextrose and 30% water).

EXAMPLE 20

| Component | Percentage | Grams |
|---|---|---|
| Maltisorb (Dry Maltitol Powder) | 54.280 | 271.40 |
| FD & C Yellow #6 HT (38%–42%) | 32.620 | 163.10 |
| FD & C Red #40 HT (38%–42%) | 3.100 | 15.50 |
| Titanium Dioxide | 10.000 | 50.00 |
|  | 100.000 | 500.00 |

The sugarless syrup solution of this example is a 70% maltitol solution (70% maltitol and 30% water).

ADVANTAGES

No preservatives are needed in the inventive dry color concentrate since the inventive dry color concentrate is dry. Accordingly, the shelf-life of the inventive dry color concentrate is longer than liquid color concentrates.

Further, less warehouse space is needed when compared with liquid color concentrates since the inventive dry color concentrate is not liquid.

Also, fewer containers of dry color concentrate are needed in order to contain the same effective amount of liquid color concentrate, and therefore, less recycling of containers is required.

The inventive dry color concentrate is less dusty than dry pigments such as lakes.

It is easier to disperse the inventive dry color concentrate into a sugar/syrup solution or a sugarless syrup solution than it is to disperse dry pigments, such as lakes, into a sugar/syrup solution or a sugarless syrup solution.

Confectionery forms coated with sugar solutions containing the inventive color concentrate have better taste and feel properties as compared with coating compositions based on hydroxypropyl methylcellulose.

Coatings made using an enhanced sugar/syrup solution of the invention and coatings made from using an enhanced sugarless syrup solution of the invention have greater film strengths than coatings made from using standard sugar/syrup solutions and standard sugarless syrup solutions.

Further, the carbohydrates (e.g. corn syrup solids) have an enhanced opacity. That is, the coatings made using an enhanced sugar/syrup solution of the invention or an enhanced sugarless syrup solution of the invention tend to be more opaque than a standard 70% sugar/syrup solution or a standard 70% sugarless syrup solution due to the presence of the carbohydrate (e.g. corn syrup solids) in our concentrate and our coating solution.

Other advantages of our invention are as follows:

1) The dry color invention is highly concentrated with colorant which results in a dramatic reduction in the amount of color product needed to color the sugar/syrup solution, which is then used to coat a substrate such as a confectionery form, pharmaceutical tablet, or the like.

2) Due to the highly concentrated nature of the dry color invention, less dry color product is needed to color sugar/syrup than the standard liquid color dispersion. This translates into lower inventory and reduced shipping costs.

3) The dry concentrate of the invention has an extended shelf life since there are no microbial concerns because the invention concentrate is stored dry.

4) Unlike known standard liquid color concentrates, there is no settling and hard packing of pigments with the inventive dry concentrate. Also, since the coating solution/dispersion made in accordance with the invention is made when needed, there is no need to redisperse pigments as may be required with known standard liquid color concentrates, and this provides more consistent color from batch to batch.

5) The invention eliminates a problem of some known standard liquid color concentrates which experience an increase in viscosity over time.

6) The inventive dry concentrate may be sold in recyclable packaging.

7) The self-opacifying properties of the carbohydrate make it possible to reduce and/or eliminate titanium dioxide in a subcoat.

8) The added opacity obtained from the carbohydrate of the invention provides an even color in the coating. The added opacity reduces mottling and blotchiness in the coating.

9) Due to the increased opacity obtained from the carbohydrates of the invention, the amount of colorant needed to color coat a substrate is less than that needed using a known standard liquid color concentrate.

10) The added opacity obtained from the carbohydrate of the invention gives brighter color in the coating.

11) The dry concentrate of the invention does not require a preservative. Accordingly, a preservative-free coating is obtained, which is especially more desirable to consumers.

12) The dry concentrate of the invention may be mixed into a sugar/syrup solution or a sugarless syrup solution using low shear agitation. The same equipment used to mix lake dispersions may be used to prepare a coating solution/dispersion of the invention.

We claim:

1. A dry color concentrate syrup modifier for adding to sugar/syrup solutions and sugarless syrup solutions used to coat confectionery forms and pharmaceutical tablets, consisting of:

a dry mixture obtained by dry blending a carbohydrate selected from the group consisting of corn syrup solids, tapioca dextrin, dextrose, sugar, polyols, and combinations thereof to enhance the sugar/syrup solutions and sugarless syrup solutions by adding opacifying and strength properties, and a colorant to enhance the sugar/syrup solutions and sugarless syrup solutions by adding a color to said syrup solutions.

2. The dry color concentrate of claim 1, further including a plasticizer.

3. The dry color concentrate syrup modifier of claim 1, wherein the carbohydrate is in a range of 12% to 100% by weight of the concentrate, and the colorant is in a range of up to 81% by weight of the concentrate.

4. The dry color concentrate syrup modifier of claim 1, wherein the carbohydrate is in a range of 35% to 65% by weight of the concentrate, and the colorant is in a range of 35% to 65% by weight of the concentrate.

5. The dry color concentrate syrup modifier of claim 2, wherein the carbohydrate is in a range of 12% to 100% by weight of the dry color concentrate, the colorant is in a range of up to 81% by weight of the dry color concentrate, and the plasticizer is in a range of up to 81% by weight of the dry color concentrate.

6. The dry color concentrate syrup modifier of claim 2, wherein the carbohydrate is in a range of 35% to 65% by weight of the dry color concentrate, the plasticizer is in a range of 5% to 6% by weight of the dry color concentrate, and the colorant is in a range of 35% to 65% by weight of the dry color concentrate.

7. The dry color concentrate syrup modifier of claim 1, wherein the colorant is FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof.

8. The dry color concentrate syrup modifier of claim 2, wherein the plasticizer is glycerin, polyethylene glycol 8000, triacetin, lecithin, or a combination thereof.

9. The dry color concentrate of claim 1, further including a plasticizer, the carbohydrate being in a range of 35% to 65% by weight of the dry color concentrate, the plasticizer being in a range of 5% to 6% by weight of the dry color concentrate, the colorant being in a range of 35% to 65% by weight of the dry color concentrate, the colorant being FD&C lakes, D&C lakes, titanium dioxide, magnesium carbonate, talc, pyrogenic silica, iron oxides, channel black, riboflavin, caramel, carmine 40, ponceau 4R, patent blue V5, caramel, curcumin, annatto, dyes, and combinations thereof, and the plasticizer being glycerin, polyethylene glycol 8000, triacetin, lecithin, or a combination thereof.

10. A method of coating an edible substrate comprising the steps of mixing a carbohydrate selected from the group consisting of corn syrup solids, maltodextrin, tapioca dextrin, dextrose, sugar, nolvols, and combinations thereof, into a sugar/syrup solution or a sugarless syrup solution to form a coating solution, applying the coating solution to the substrate to form a coating thereon, and drying the coating.

11. The method of claim 10, further including the step of mixing a colorant into the sugar/syrup solution or the sugarless syrup solution.

12. The method of claim 10, further including the step of mixing a plasticizer into the sugar/syrup solution or the sugarless syrup solution.

13. The method of claim 10, further including the step of mixing a colorant and a plasticizer into the sugar/syrup solution or the sugarless syrup solution.

14. The method of claim 11, the carbohydrate being in a range of 12% to 100% by weight of the ingredients added to the sugar/syrup solution or to the sugarless syrup solution, and the colorant being in a range of up to 81% by weight of the ingredients added to the sugar/syrup solution or to the sugarless syrup solution.

15. The method of claim 11, wherein the carbohydrate is in a range of 35% to 65% by weight of the ingredients added to the sugar/syrup solution or to the sugarless syrup solution, and the colorant is in a range of 35% to 65% by weight of the ingredients added to the sugar/syrup solution or to the sugarless syrup solution.

16. The method of claim 12, wherein the carbohydrate is in a range of 12% to 100% by weight of the ingredients added to the sugar/syrup solution or to the sugarless syrup solution, and the plasticizer is in a range of up to 81% by weight of the ingredients added to the sugar/syrup solution or to the sugarless syrup solution.

17. The method of claim 12, wherein the carbohydrate is in a range of 81% to 100% by weight of the ingredients added to the sugar/syrup solution or to the sugarless syrup solution, and the plasticizer is in a range of up to 19% by weight of the ingredients added to the sugar/syrup solution or to the sugarless syrup solution.

18. The method of claim 12, wherein the carbohydrate is in a range of about 94% to about 95% by weight of the ingredients added to the sugar/syrup solution or to the sugarless syrup solution, and the plasticizer is in a range of about 5% to about 6% by weight of the ingredients added to the sugar/syrup solution or to the sugarless syrup solution.

19. The method of claim 13, wherein the carbohydrate is in a range of 12% to 100% by weight of the ingredients added to the sugar/syrup solution or to the sugarless syrup solution, the colorant is in a range of up to 81% by weight of the ingredients added to the sugar/syrup solution or to the sugarless syrup solution, and the plasticizer is in a range of up to 81% by weight of the ingredients added to the sugar/syrup solution or to the sugarless syrup solution.

20. The method of claim 13, wherein the carbohydrate is in a range of 35% to 65% by weight of the ingredients added to the sugar/syrup solution or to the sugarless syrup solution, the plasticizer is in a range of 5% to 6% by weight of the ingredients added to the sugar/syrup solution or to the sugarless syrup solution, and the colorant is in a range of 35% to 65% by weight of the ingredients added to the sugar/syrup solution or to the sugarless syrup solution.

21. The method of claim 11, wherein the colorant is FD&C lakes, D&C lakes, titanium dioxide, magnesium carbonate, talc, pyrogenic silica, iron oxides, channel black, riboflavin, caramel, carmine 40, ponceau 4R, patent blue V5, caramel, curcumin, annatto, dyes, and combinations thereof.

22. The method of claim 12, wherein the plasticizer is glycerin, polyethylene glycol 8000, triacetin, lecithin, or a combination thereof.

23. The method of claim 19, wherein the colorant is FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof, and the plasticizer is glycerin, polyethylene glycol 8000, triacetin, lecithin, or a combination thereof.

24. The method of claim 20, wherein the colorant is FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof, and the plasticizer is glycerin, polyethylene glycol 8000, triacetin, lecithin, or a combination thereof.

25. A dry concentrate syrup modifier for mixing into a sugar/syrup solution or a sugarless syrup solution used to coat confectionery forms and pharmaceutical tablets, consisting of:

a carbohydrate selected from the group consisting of corn syrup solids, tapioca dextrin, dextrose, sugar, polyols, and combinations thereof to enhance to sugar/syrup solutions and sugarless syrup solutions by adding opacifying and strength properties, and a plasticizer.

26. The dry concentrate of claim 25, wherein the carbohydrate is in a range of 12% to 100% by weight of the dry concentrate, and the plasticizer is in a range of up to 81% by weight of the dry concentrate.

27. The dry concentrate of claim 25, wherein the carbohydrate is in a range of 81% to 100% by weight of the dry concentrate, and the plasticizer is in a range of up to 19% by weight of the dry concentrate.

28. The dry concentrate of claim 25, wherein the plasticizer is glycerin, polyethylene glycol 8000, triacetin, lecithin, or a combination thereof.

29. The dry concentrate of claim 25, wherein the carbohydrate is in a range of 19% to 100% by weight of the dry concentrate, and the plasticizer is in a range of up to 81% by weight of the dry concentrate, the plasticizer is glycerin, polyethylene glycol 8000, triacetin, lecithin, or a combination thereof.

30. The dry concentrate of claim 25, wherein the carbohydrate is in a range of 81% to 100% by weight of the dry concentrate, and the plasticizer is in a range of up to 19% by weight of the dry concentrate, and the plasticizer is glycerin, polyethylene glycol 8000, triacetin, lecithin, or a combination thereof.

31. The dry concentrate of claim 25, wherein the carbohydrate is in a range of about 94% to about 95% by weight of the dry concentrate, and the plasticizer is in a range of about 5% to about 6% by weight of the dry concentrate, and the plasticizer is glycerin, polyethylene glycol 8000, triacetin, lecithin, or a combination thereof.

32. A dry color concentrate syrup modifier for adding to sugar/syrup solutions and sugarless syrup solutions used to coat confectionery forms, and pharmaceutical tablets, consisting of:

a dry mixture obtained by dry blending a carbohydrate selected from the group consisting of corn syrup solids, maltodextrin, tapioca dextrin, dextrose, sugar, polyols, and combinations thereof to enhance to sugar/syrup solutions and sugarless syrup solutions by adding opacifying and strength properties, and a colorant to enhance the sugar/syrup solutions and the sugarless syrup solutions by adding a color to said syrup solutions.

33. The dry color concentrate syrup modifier of claim 32, further including a plasticizer.

34. The dry color concentrate syrup modifier of claim 32, wherein the carbohydrate is in a range of 12% to 100% by weight of the concentrate, and the colorant is in a range of up to 81% by weight of the concentrate.

35. The dry color concentrate syrup modifier of claim 32, wherein the carbohydrate is in a range of 35% to 65% by weight of the concentrate, and the colorant is in a range of 35% to 65% by weight of the concentrate.

36. The dry color concentrate syrup modifier of claim 33, wherein the carbohydrate is in a range of 12% to 100% by weight of the dry color concentrate, the colorant is in a range of up to 81% by weight of the dry color concentrate, and the plasticizer is in a range of up to 81% by weight of the dry color concentrate.

37. The dry color concentrate syrup modifier of claim 33, wherein the carbohydrate is in a range of 35% to 65% by weight of the dry color concentrate, the plasticizer is in a range of 5% to 6% by weight of the dry color concentrate, and the colorant is in a range of 35% to 65% by weight of the dry color concentrate.

38. The dry color concentrate syrup modifier of claim 32, wherein the colorant is FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof.

39. The dry color concentrate syrup modifier of claim 33, wherein the plasticizer is glycerin, polyethylene glycol 8000, triacetin, lecithin, or a combination thereof.

40. The dry color concentrate syrup modifier of claim 32, further including a plasticizer, the carbohydrate being in a range of 35% to 65% by weight of the dry color concentrate, the plasticizer being in a range of 5% to 6% by weight of the dry color concentrate, the colorant being in a range of 35% to 65% by weight of the dry color concentrate, the colorant being FD&C lakes, D&C lakes, titanium dioxide, magnesium carbonate, talc, pyrogenics silica, iron oxides, channel black, riboflavin, caramel, carmine 40, ponceau 4R, patent blue V5, caramel, curcumin, annatto, dyes, and combinations thereof, and the plasticizer being glycerin, polyethylene glycol 8000, triacetin, lecithin, or a combination, thereof.

41. A method of coating confectionery forms, and pharmaceutical tablets,consisting essentially of the steps of mixing a carbohydrate selected from the group consisting of corn syrup solids, maltodextrin, tapioca dextrin, dextrose, sugar, polyols, and combinations thereof, into a sugar/syrup solution or a sugarless syrup solution to form a coating solution, applying the coating solution to the confectionery forms or pharmaceutical tablets to form a coating thereon, and drying the coating.

42. The method of claim 41, further including the step of mixing a colorant into the sugar/syrup solution or the sugarless syrup solution.

43. The method of claim 41, further including the step of mixing a plasticizer into the sugar/syrup solution or the sugarless syrup solution.

44. The method of claim 41, further including the step of mixing a colorant and a plasticizer into the sugar/syrup solution or the sugarless syrup solution.

45. The method of claim 42, wherein the carbohydrate is in a range of 12% to 100% by weight of the ingredients added to the sugar/syrup solution or to the sugarless syrup solution, and the colorant is in a range of up to 81% by weight of the ingredients added to the sugar/syrup solution or to the sugarless syrup solution.

46. The method of claim 42, wherein the carbohydrate is in a range of 35% to 65% by weight of the ingredients added to the sugar/syrup solution or to the sugarless syrup solution, and the colorant is in a range of 35% to 65% by weight of the ingredients added to the sugar/syrup solution or to the sugarless syrup solution.

47. The method of claim 43, wherein the carbohydrate is in a range of 12% to 100% by weight of the ingredients added to the sugar/syrup solution or to the sugarless syrup solution, and the plasticizer is in a range of up to 81% by weight of the ingredients added to the sugar/syrup solution or to the sugarless syrup solution.

48. The method of claim 43, wherein the carbohydrate is in a range of 81% to 100% by weight of the ingredients added to the sugar/syrup solution or to the sugarless syrup solution, and the plasticizer is in a range of up to 19% by weight of the ingredients added to the sugar/syrup solution or to the sugarless syrup solution.

49. The method of claim 43, wherein the carbohydrate is in a range of about 94% to about 95% by weight of the ingredients added to the sugar/syrup solution or to the sugarless syrup solution, and the plasticizer is in a range of about 5% to about 6% by weight of the ingredients added to the sugar/syrup solution or to the sugarless syrup solution.

50. The method of claim 44, wherein the,carbohydrate is in a range of 12% to 100% by weight of the ingredients added to the sugar/syrup solution or to the sugarless syrup solution, the colorant is in a range of up to 81% by weight of the ingredients added to the sugar/syrup solution or to the sugarless syrup solution, and the plasticizer is in a range of up to 81% by weight of the ingredients added to the sugar/syrup solution or to the sugarless syrup solution.

51. The method of claim 44, wherein the carbohydrate is in a range of 35% to 65% by weight of the ingredients added to the sugar/syrup solution or to the sugarless syrup solution, the plasticizer is in a range of 5% to 6% by weight of the ingredients added to the sugar/syrup solution or to the sugarless syrup solution, and the colorant is in a range of 35% to 65% by weight of the ingredients added to the sugar/syrup solution or to the sugarless syrup solution.

52. The method of claim 42, wherein the colorant is FD&C lakes, D&C lakes, titanium dioxide, magnesium carbonate, talc, pyrogenic silica, iron oxides, channel black, riboflavin, caramel, carmine 40, ponceau 4R, patent blue V5, caramel, curcumin, annatto, dyes, and combinations thereof.

53. The method of claim 43, wherein the plasticizer is glycerin, polyethylene glycol 8000, triacetin, lecithin, or a combination thereof.

54. The method of claim 50, wherein the colorant is FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof, and the plasticizer is glycerin, polyethylene glycol 8000, triacetin, lecithin, or a combination thereof.

55. The method of claim 51, wherein the colorant is FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof, and the plasticizer is glycerin, polyethylene glycol 8000, triacetin, lecithin, or a combination thereof.

56. A dry concentrate syrup modifier for mixing into a sugar/syrup solution or a sugarless syrup solution used to coat confectionery forms, and pharmaceutical tablets, consisting of:

a carbohydrate selected from the group consisting of corn syrup solids, maltodextrin, tapioca dextrin, dextrose, sugar, polyols, and combinations thereof to enhance to sugar/syrup solutions and sugarless syrup solutions by adding opacifyina and strength properties, and a plasticizer.

57. The dry concentrate syrup modifier of claim 56, wherein the carbohydrate is in a range of 12% to 100% by weight of the dry concentrate, and the plasticizer is in a range of up to 81% by weight of the dry concentrate.

58. The dry concentrate syrup modifier of claim 56, wherein the carbohydrate is in a range of 81% to 100% by weight of the dry concentrate, and the plasticizer is in a range of up to 19% by weight of the dry concentrate.

59. The dry concentrate syrup modifier of claim 56, wherein the plasticizer is glycerin, polyethylene glycol 8000, triacetin, lecithin, or a combination thereof.

60. The dry concentrate syrup modifier of claim 56, wherein the carbohydrate is in a range of 19% to 100% by weight of the dry concentrate, the plasticizer is in a range of up to 81% by weight of the dry concentrate, and the plasticizer is glycerin, polyethylene glycol 8000, triacetin, lecithin, or a combination thereof.

61. The dry concentrate syrup modifier of claim 56, wherein the carbohydrate is in a range of 81% to 100% by weight of the dry concentrate, the plasticizer is in a range of up to 19% by weight of the dry concentrate, and the plasticizer is glycerin, polyethylene glycol 8000, triacetin, lecithin, or a combination thereof.

62. The dry concentrate syrup modifier of claim 56, wherein the carbohydrate is in a range of about 94% to about 95% by-weight of the dry concentrate, the plasticizer is in a range of about 5% to about 6% by weight of the dry concentrate, and the plasticizer is glycerin, polyethylene glycol 8000, triacetin, lecithin, or a combination thereof.

63. A dry color concentrate syrup modifier for use in coloring sugar/syrup solutions and sugarless syrup solutions used to coat confectionery forms, and pharmaceutical tablets, consisting of:

corn syrup solids to enhance to sugar/syrup solutions and sugarless syrup solutions by adding opacifying and strength properties, a colorant to enhance the sucrar/syrup solutions and the sugarless syrup solutions by adding a color to said syrup solutions, and a plasticizer.

* * * * *